United States Patent
Johnson

(10) Patent No.: US 9,358,142 B2
(45) Date of Patent: Jun. 7, 2016

(54) CATHETER HAVING GUIDEWIRE CHANNEL

(75) Inventor: Eric Gerard Johnson, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 511 days.

(21) Appl. No.: 11/739,169

(22) Filed: Apr. 24, 2007

(65) Prior Publication Data

US 2008/0269867 A1    Oct. 30, 2008

(51) Int. Cl.
| | | |
|---|---|---|
| *A61F 2/06* | (2013.01) | |
| *A61F 2/97* | (2013.01) | |
| *A61F 2/07* | (2013.01) | |
| *A61F 2/954* | (2013.01) | |
| *A61F 2/856* | (2013.01) | |
| *A61F 2/82* | (2013.01) | |

(52) U.S. Cl.
CPC ... *A61F 2/97* (2013.01); *A61F 2/07* (2013.01); *A61F 2/954* (2013.01); *A61F 2/856* (2013.01); *A61F 2002/061* (2013.01); *A61F 2002/065* (2013.01); *A61F 2002/075* (2013.01); *A61F 2002/821* (2013.01); *A61F 2250/0059* (2013.01)

(58) Field of Classification Search
CPC .................................. A61F 2/95–2/97; A61F 2002/9505–2002/9665
USPC ....................... 623/1.11, 1.12, 1.23
See application file for complete search history.

(56) References Cited

U.S. PATENT DOCUMENTS

| | | | | |
|---|---|---|---|---|
| 5,755,769 | A * | 5/1998 | Richard et al. | 623/1.2 |
| 6,042,605 | A | 3/2000 | Martin et al. | 623/1 |
| 6,264,682 | B1 * | 7/2001 | Wilson et al. | 623/1.11 |
| 6,352,561 | B1 * | 3/2002 | Leopold et al. | 623/1.23 |
| 6,361,544 | B1 | 3/2002 | Wilson et al. | |
| 6,361,637 | B2 | 3/2002 | Martin et al. | 156/187 |
| 6,520,986 | B2 | 2/2003 | Martin et al. | 623/1.13 |
| 6,520,988 | B1 * | 2/2003 | Colombo et al. | 623/1.35 |
| 6,551,350 | B1 | 4/2003 | Thornton et al. | 623/1.13 |
| 6,645,242 | B1 * | 11/2003 | Quinn | 623/1.16 |
| 6,682,556 | B1 * | 1/2004 | Ischinger | 623/1.35 |
| 6,890,349 | B2 * | 5/2005 | McGuckin et al. | 623/1.13 |
| 6,908,477 | B2 * | 6/2005 | McGuckin et al. | 623/1.11 |
| 6,962,602 | B2 * | 11/2005 | Vardi et al. | 623/1.11 |
| 7,537,606 | B2 | 5/2009 | Hartley et al. | |
| 2002/0173835 | A1 * | 11/2002 | Bourang et al. | 623/1.11 |
| 2003/0055483 | A1 * | 3/2003 | Gumm | 623/1.11 |
| 2004/0093067 | A1 * | 5/2004 | Israel | A61F 2/856 623/1.15 |
| 2004/0102719 | A1 | 5/2004 | Keith et al. | |
| 2004/0133130 | A1 | 7/2004 | Ferry et al. | |
| 2004/0143286 | A1 * | 7/2004 | Johnson et al. | 606/194 |
| 2004/0153136 | A1 | 8/2004 | Vardi et al. | |
| 2004/0172121 | A1 * | 9/2004 | Eidenschink et al. | 623/1.11 |
| 2004/0199073 | A1 | 10/2004 | Ma | |
| 2005/0038494 | A1 * | 2/2005 | Eidenschink | 623/1.11 |

(Continued)

FOREIGN PATENT DOCUMENTS

| | | |
|---|---|---|
| EP | 1 512 380 | 3/2005 |
| WO | 99/34749 | 7/1999 |
| WO | 00/74595 | 12/2000 |

(Continued)

*Primary Examiner* — Katherine Rodjom
*Assistant Examiner* — Jonathan Hollm

(57) ABSTRACT

Catheter for delivering an expandable prosthetic device. The catheter has a guidewire channel for delivering a side branch guidewire to a side branch target site. An expandable prosthetic device can be loaded on to the distal end of the catheter.

16 Claims, 12 Drawing Sheets

(56) References Cited

U.S. PATENT DOCUMENTS

| | | |
|---|---|---|
| 2005/0187602 A1 | 8/2005 | Eidenschink |
| 2006/0041303 A1 | 2/2006 | Israel |
| 2006/0074475 A1* | 4/2006 | Gumm .................. 623/1.11 |
| 2006/0100694 A1* | 5/2006 | Globerman ............. 623/1.35 |
| 2006/0287712 A1 | 12/2006 | Eidenschink |
| 2007/0083215 A1 | 4/2007 | Hamer et al. |
| 2007/0106245 A1 | 5/2007 | McQueen et al. |

FOREIGN PATENT DOCUMENTS

| | | |
|---|---|---|
| WO | 2005/025458 | 3/2005 |
| WO | 2005/025468 | 3/2005 |
| WO | 2007/001519 | 1/2007 |
| WO | 02/30329 | 4/2007 |

* cited by examiner

CATHETER HAVING GUIDEWIRE CHANNEL

FIELD OF THE INVENTION

The present invention relates to catheters useful for delivering expandable endoluminal prostheses. The catheters are particularly suited for use in delivering expandable endoluminal prostheses to bifurcated regions of body lumens.

BACKGROUND OF THE INVENTION

Stents or stent grafts are examples of expandable endoluminal prosthetic devices which are used to maintain, open or dilate stenotic lesions in body lumens or to cover and repair an aneurysm. Vascular disease may occur at a branch or bifurcation in a vessel. Placement and deployment of these prosthetic devices at bifurcations can often be problematic. One current technique is to initially deploy across an aneurysm a main body prosthetic device having a side wall opening. The side wall opening is aligned with the side branch ostium. A second prosthetic device is then deployed through the main body prosthetic device side wall opening and into the side branch vessel. Procedural complications are often encountered while practicing this technique. These complications typically relate to the accurate placement of the main body prosthetic device and in particular to the precise alignment of the side wall opening to the native side branch vessel. Subsequent placement of the side branch guidewire through the main body prosthetic device, through the side wall opening and then into the side branch vessel can also be problematic. The deployment of the side branch prosthetic device into the native vessel can present problems relating to the longitudinal placement of the device.

Alternate procedures for treating bifurcated vessels place the guidewires prior to the device deployments. After the main body prosthetic device is deployed it is advantageous to then remove the main body delivery catheter prior to the delivery of the side branch prosthetic device. Typical delivery systems incorporate guidewires that are contained or captured within the delivery catheter. The catheter removal therefore requires careful management of the side branch guidewire to prevent its dislodgement during the removal of the delivery catheter.

SUMMARY OF THE INVENTION

An aspect of the invention includes a catheter comprising:
Catheter body having a proximal portion, a distal portion, a proximal end, and a distal end; and
At least one guidewire channel having a proximal end and a distal end, the at least one guidewire channel having a longitudinal opening therein extending from the channel proximal end to the channel distal end, the proximal end of the at least one guidewire channel being attached to the catheter body at the distal portion of the catheter body.

The catheter body can include a guidewire lumen extending from the catheter body distal end to a point proximal thereto.

Further, an expandable prosthesis can be loaded on the distal end of the catheter, with the guidewire channel proximal end extending proximally from the expandable prosthesis and the guidewire channel distal end extending out of a side opening in the expandable prosthesis.

A further aspect of the invention provides methods for delivering an expandable prosthesis using the catheter of the invention that overcome the drawbacks relating to conventional devices and delivery methods.

DETAILED DESCRIPTION OF THE INVENTION

An aspect of the invention includes a catheter comprising:
Catheter body having a proximal portion, a distal portion, a proximal end, and a distal end; and
At least one guidewire channel having a proximal end and a distal end, the at least one guidewire channel having a longitudinal opening therein extending from the channel proximal end to the channel distal end, the proximal end of the at least one guidewire channel being attached to the catheter body at the distal portion of the catheter body.

The catheter body can include a guidewire lumen extending from the catheter body distal end to a point proximal thereto.

Further, an expandable prosthesis can be loaded on the distal end of the catheter, with the guidewire channel proximal end extending proximally from the expandable prosthesis and the guidewire channel distal end extending out of a side opening in the expandable prosthesis.

A further aspect of the invention provides methods for delivery of an expandable prosthesis that overcome the drawbacks relating to conventional devices and delivery methods. The present invention allows for the initial placement of multiple guidewires into selected target sites. The guidewire placement is simplified since there are no endoluminal devices complicating the guidewire placement. As a failsafe, the procedure can be aborted if the guidewires cannot be properly placed. After proper placement of the guidewires is confirmed, a main body, expandable prosthetic device can be advanced to the treatment site. This main body device has a separate side branch guidewire that passes through the main body device and through the side opening in the main body device. Therefore as the main body device is advanced, the side opening is self guided (by the side branch guidewire) and self aligns to the side branch vessel ostium. The main body device is then deployed, leaving the side branch guidewire in place. The side branch guidewire is released from the catheter as the main body device is deployed. The delivery catheter can then be readily removed without dislodging the placement of the side branch guidewire. A side branch prosthetic device can then be advanced along the side branch guidewire through the main body device, through the side wall opening and into the native side branch vessel. The side branch device can then be deployed to engage the main body device and the native side branch vessel.

Further understanding of the invention may be had with reference to the figures. Shown in FIG. 1 is a catheter according to the present invention.

Figure 1:
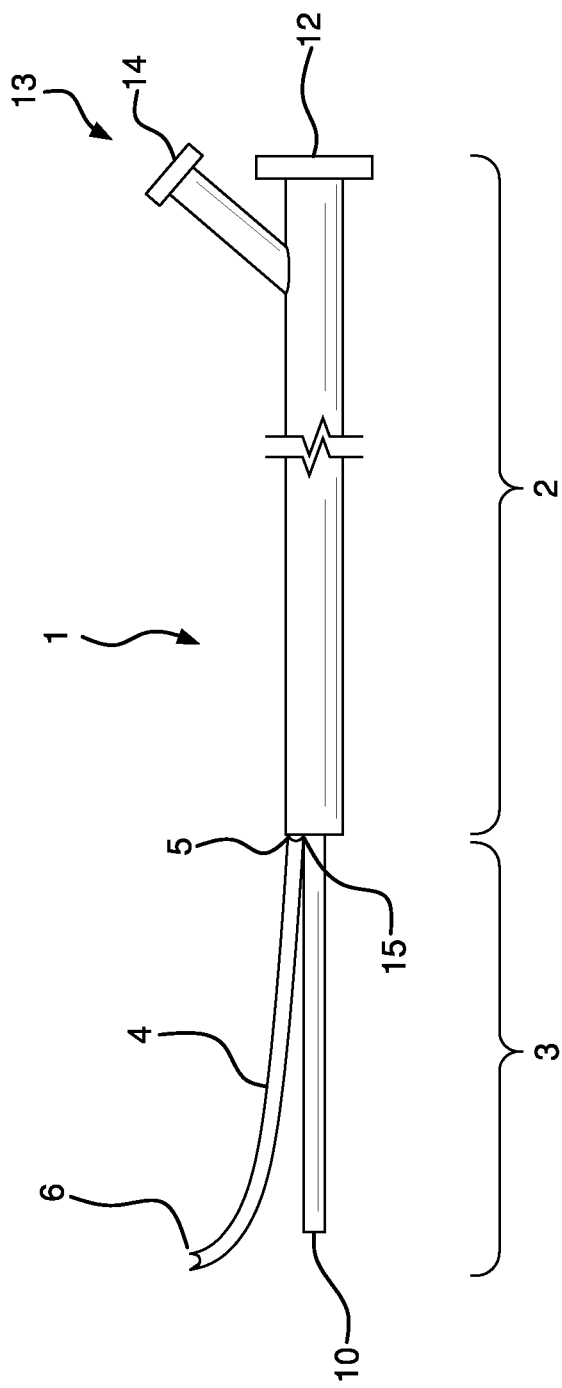
FIG. 1 is a side view of a catheter according to an aspect of the invention.

FIG. 1 shows a catheter 1 having a proximal portion 2, a distal portion 3, and a guidewire channel 4. The guidewire channel has a distal end 6 and a proximal end 5. As is shown, the guidewire channel has an essentially C-shaped cross-section. The proximal end 5 is attached to the distal end 3 of the catheter at 15. Catheter 1 can include an optional guidewire lumen extending from the distal tip 10 to the proximal end 12 of the catheter assembly. The catheter assembly can further include proximal hub assembly 13.

The catheter may further include an expandable prosthesis loaded on the distal portion thereof.

The expandable prosthesis comprises a first open end and a second open end, a wall extending from the first open end to the second open end, and at least one side opening in the wall.

The expandable prosthesis can be either self-expanding or balloon expandable. Typically, a self-expanding prosthesis will comprise at least one shape memory material, such as nitinol. The expandable prosthesis can comprise a stent or stent graft. Suitable stent materials include, in addition to nitinol, for example, metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

The expandable prosthesis can comprise a stent at either the first open end, the second open end, or at both the first open end and the second open end. Moreover, the stent can be a single stent extending from the first open end to the second open end. In an aspect of the invention, graft material is used to form the wall and extends from the first open end to the second open end of the expandable prosthesis. Grafts can have various configurations and can be fabricated, for example, from tubes, sheets or films formed into tubular shapes, woven or knitted fibers or ribbons or combinations thereof. Graft materials can include conventional medical grade materials such as nylon, polyester, polyethylene, polypropylene, polytetrafluoroethylene, polyurethane and elastomeric organosilicon polymers.

Stents can be used alone or in combination with graft materials. Stents can be configured on the external or internal surface of a graft or may be incorporated into the internal wall structure of a graft.

Figure 2:
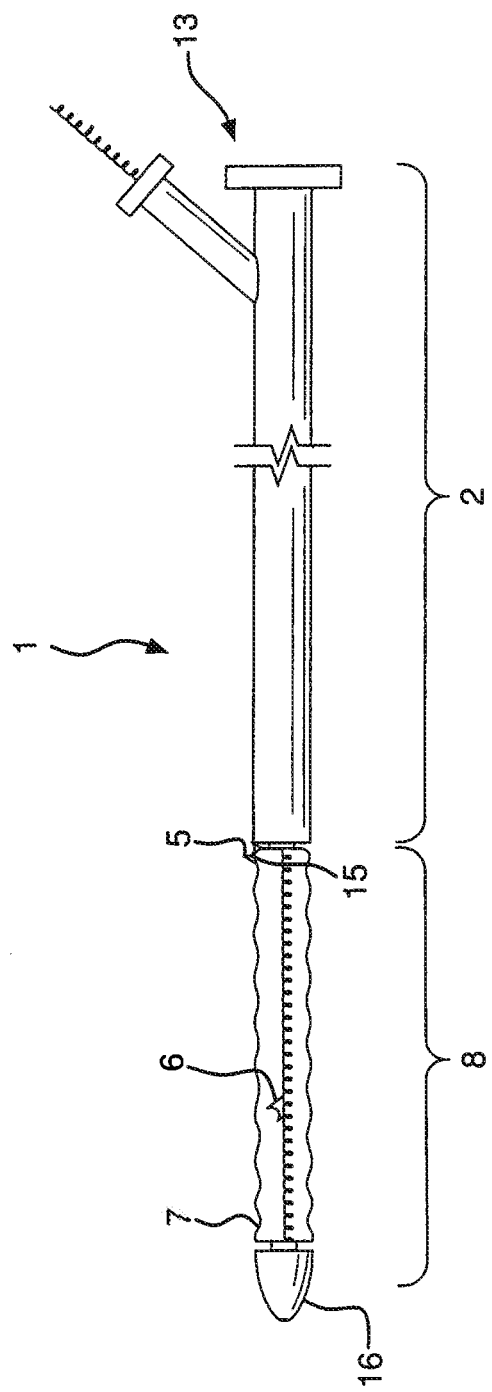
FIG. 2 is a side view of a catheter assembly having an expandable prosthetic device loaded on the distal portion thereof.

FIG. 2 is a side view of a catheter assembly 1 having a proximal catheter portion 2 and a proximal hub assembly 13. Loaded on the distal catheter portion is an expandable stent (or stent graft) 8. The expandable stent 8 is shown in a compressed state, maintained by a constraining sleeve 7. Also shown is distal end 6 of the guidewire channel extending out of a side opening in the stent 8, and proximal end 5 of the guidewire channel extending from the proximal end of stent 8 and being attached to the distal end of the catheter at 15.

Figure 3:
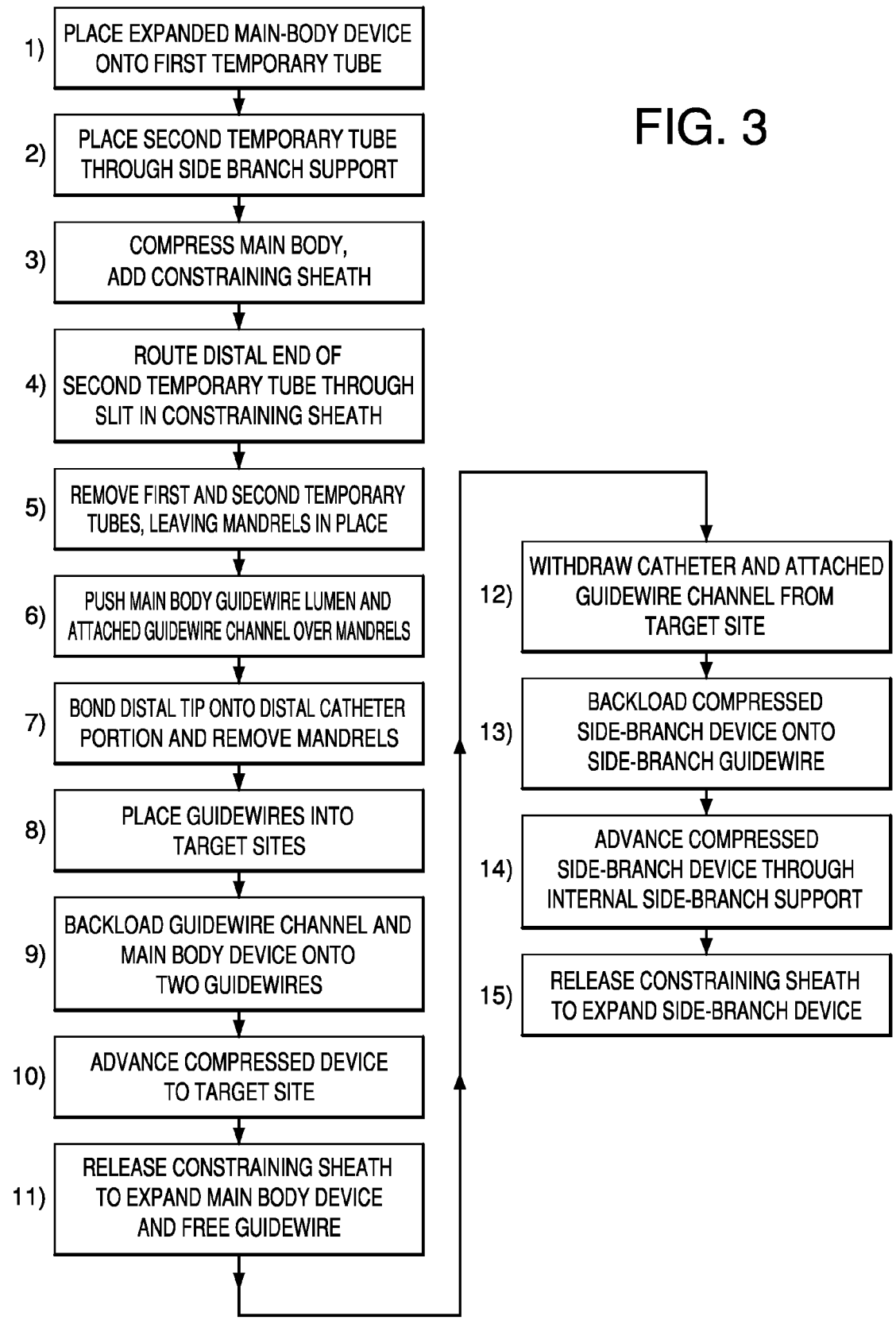
FIG. 3 is a flow chart listing the process steps used for the fabrication and delivery of a catheter assembly according to an aspect of the invention.

FIG. 3 is a flow chart depicting the assembly and delivery sequence of a catheter having a guidewire channel according to an aspect of the invention. Following are details relating to the steps listed on flowchart FIG. 3:

Step 1) Place Expanded Main-Body Device onto First Temporary Tube.

Figure 4:
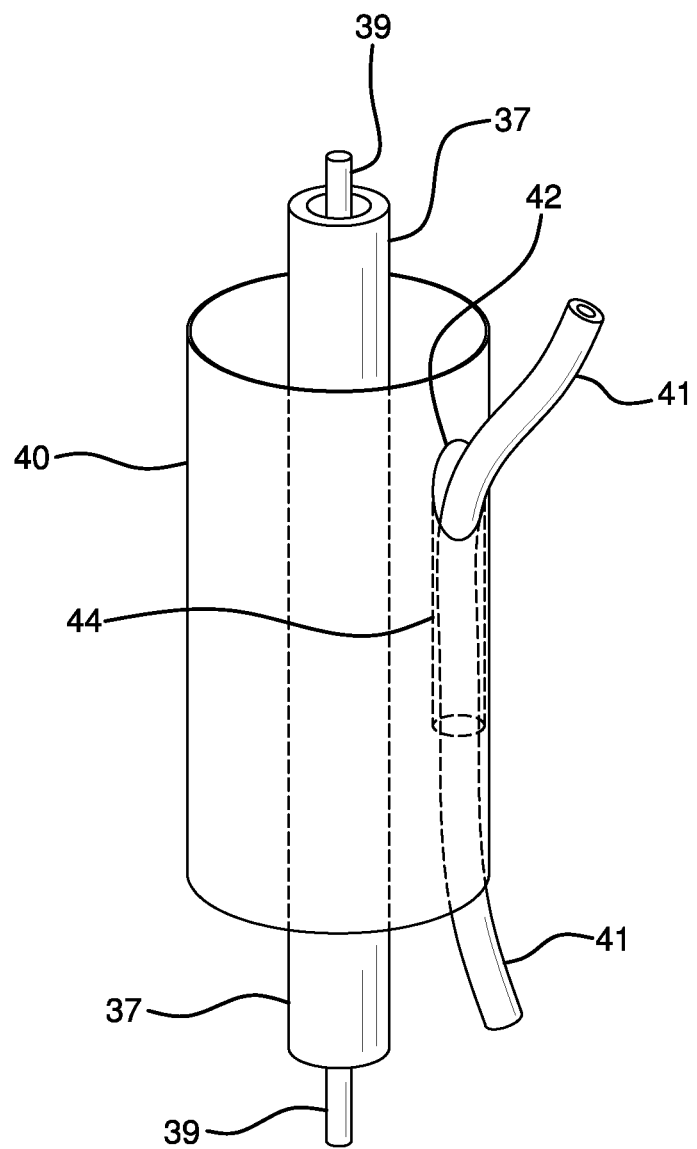
FIG. 4 is a perspective view of an expanded main body stent graft with first temporary tube routed through the main body lumen and a second temporary tube routed through a side branch support.

Shown in FIG. 4 is an expanded main body stent graft 40 having a side wall opening 42 and an internal side branch support 44. A first temporary tube 37 can be inserted through the stent graft main body lumen. A first stiffening mandrel 39 can be positioned within the first temporary tube. The stent graft can be fabricated according to the methods and materials as generally disclosed in U.S. Pat. Nos. 6,042,605, 6,361,637, and 6,520,986, all to Martin et al. Details relating to the fabrication and materials used for an internal side branch support tube can be found in U.S. Pat. No. 6,645,242, to Quinn.

Step 2) Place Second Temporary Tube Through Side Branch Support.

Referring to FIG. 4, a second temporary tube 41 can be routed through the side wall opening 42 and through the internal side branch support 44.

Step 3) Compress Main Body, Add Constraining Sheath

Figure 5B:
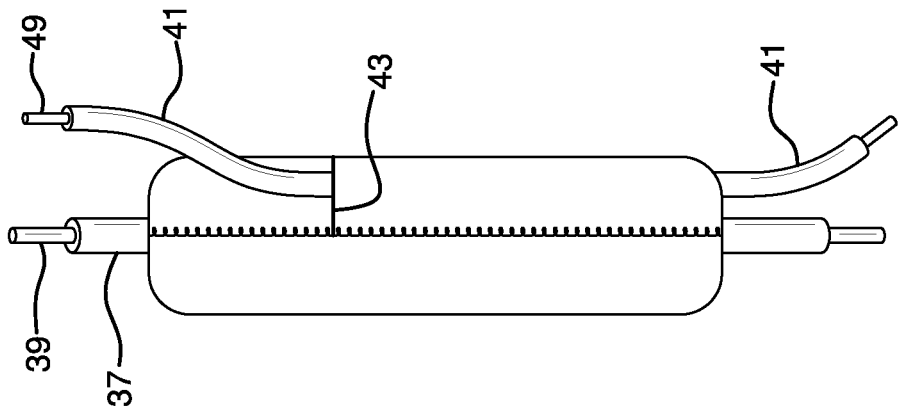
FIGS. 5A and 5B are perspective views of a compressed and constrained main body stent graft displaying the routing of two temporary tubes.
Figure 5A:
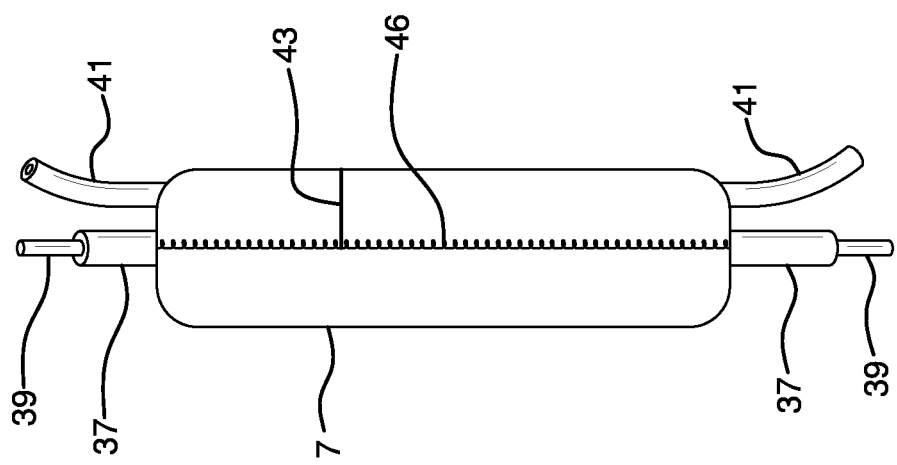

Referring to FIG. 5A, the main body stent (40, FIG. 4) can be compressed and held in the compressed state by a constraining sheath 7. The sheath can be laced together by a deployment cord 46. The sheath lacing forms a generally longitudinal seam along the constraining sheath. The constraining sheath can be provided with a slit 43 that is oriented perpendicular to the longitudinal seam formed by deployment cord 46. The slit will subsequently provide an exit point for the second temporary tube 41. Details relating to constraining sheath materials, sheath methods of manufacture and main body compression techniques can be found, for example, in U.S. Pat. No. 6,352,561 to Leopold et al., and U.S. Pat. No. 6,551,350 Thornton et al.

Step 4) Route Distal End of Second Temporary Tube Through Slit in Constraining Sheath.

As shown in FIG. 5B, the second temporary tube 41 can be routed through the slit 43. A small spring puller or hook can be inserted through the slit and be used to engage the lumen of the second temporary tube. Once the lumen is engaged the second tube can be pulled through the slit as shown in FIG. 5B. After the second temporary tube 41 is routed through the constraining sheath, a second stiffening mandrel 49 can be inserted through the second temporary tube.

Step 5) Remove First and Second Temporary Tubes, Leaving Both Stiffening Mandrels in Place.

The two temporary tubes 37 and 41 can be removed, leaving the two stiffening mandrels 39 and 49 in place.

Step 6) Push Main Body Guidewire Lumen and Attached Guidewire Channel Over Mandrels.

Referring to FIG. 1, a catheter 1 can be provided having a proximal portion 2 and a distal portion 3. A hub assembly 13 can be attached to the proximal catheter portion 2. The hub assembly 13 has a main guidewire lumen extending from the proximal end 12, through the hub assembly, to the distal end 10 of the catheter 1. Also shown is a deployment cord lumen 14. The distal catheter portion 3 is shown having a guidewire channel 4 that is attached to the catheter at the juncture 15. The distal portion of the guidewire lumen can be placed onto the first stiffening mandrel 39 while the attached guidewire channel 4 is simultaneously placed onto the second stiffening mandrel 49. The catheter assembly can then be fully advanced so that the guidewire lumen and the attached guidewire channel 4 are driven through the compressed device.

Step 7) Bond Distal Tip onto Distal Catheter Portion and Remove Mandrels.

A compliant tip 16 can then be molded onto the distal end of catheter 1, as shown in FIG. 2. The distal end 6 of the guidewire channel 4 can then be trimmed to length.

The catheter and hub can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers, Pebax® polyether block amide, and metals such as stainless steels and nitinol.

The proximal and distal catheter portions can have diameters and lengths suitable for the delivery of a variety of stent configurations. Catheter diameters can range from about 1 mm to over 20 mm, with a preferred range of about 2 mm to about 15 mm, with a most preferred range of about 2 mm to about 6 mm. Catheter lengths can vary from about 20 cm to over 100 cm. Lengths of distal catheter portions can vary from about 5 cm to over 20 cm.

Materials useful as catheter and hub materials are also useful for fabricating the guidewire channel.

The device can then be delivered and implanted according to the following procedure.

Step 8) Place Guidewires into Target Sites

Figure 6:
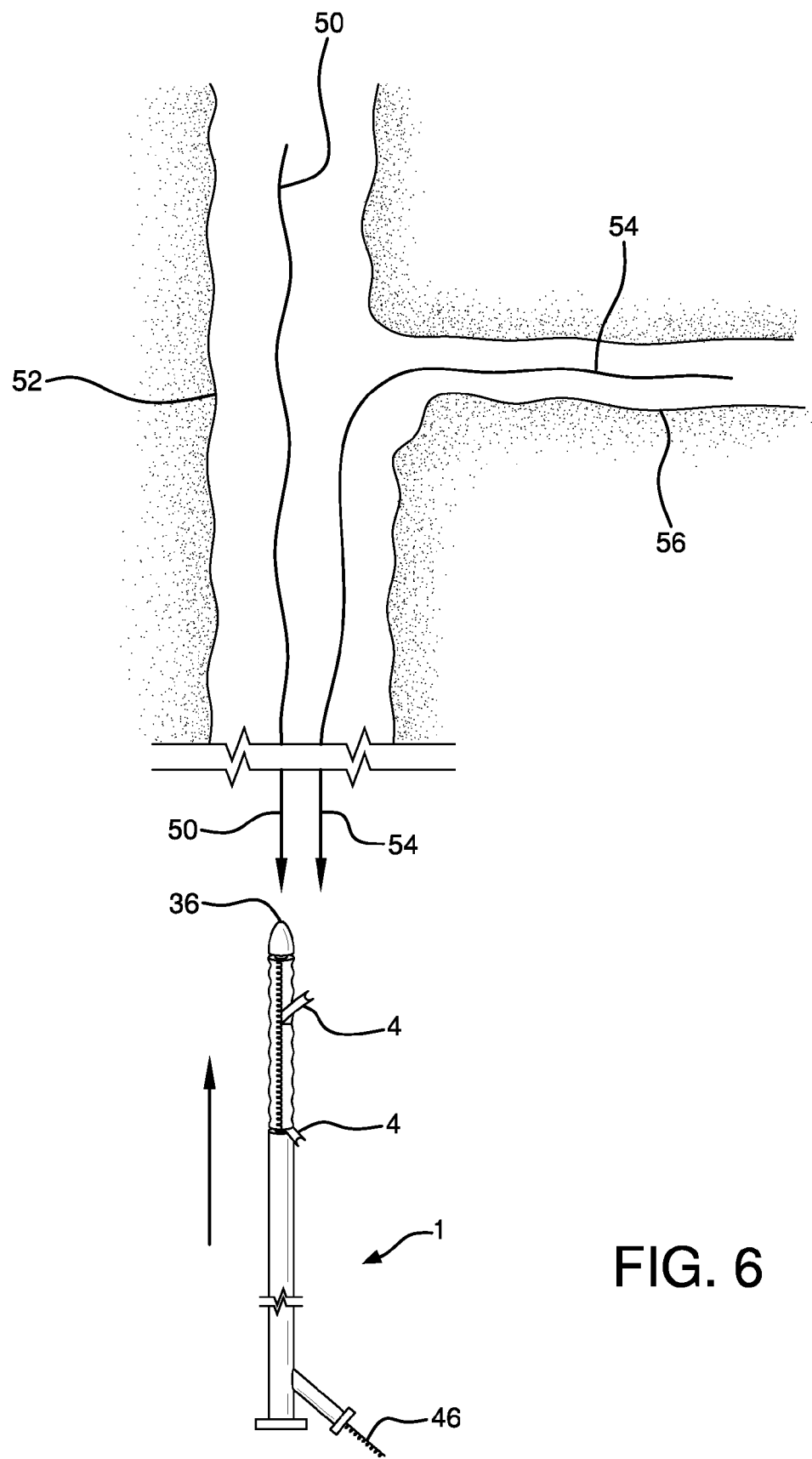
FIG. 6 is a schematic diagram showing pre-placed guidewires loaded through a compressed device with a removable guidewire tube.

As shown in FIG. 6, two guidewires can be placed into native vessels. Shown are a main body guidewire 50 placed into a main vessel 52 and a side branch guidewire 54 placed into a side branch vessel 56. An introducer sheath (not shown) can be used during the guidewire placement. A hemostatic valve (not shown) is typically used to control back-bleeding during the guidewire and subsequent device placement. Typical guidewires (with 0.035" and 0.014" diameters) can be used.

Step 9) Backload Guidewire Channel and Main Body Device onto Two Guidewires.

Figure 7:
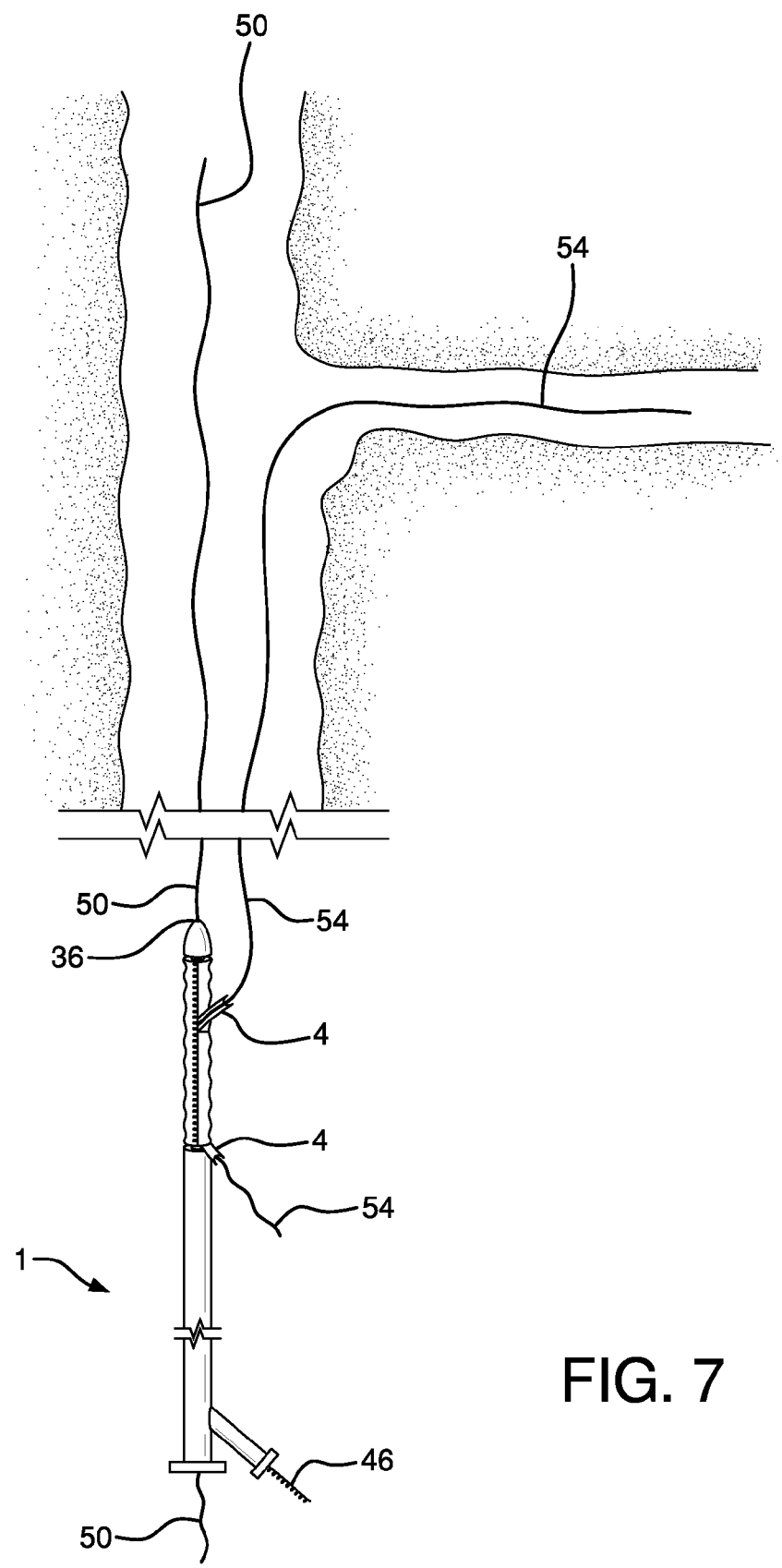
FIG. 7 is a schematic diagram showing a main guidewire routed through a catheter main lumen and a side branch guidewire routed through a guidewire channel.

As further shown in FIG. 7, the catheter assembly 1 can be back loaded onto the two guidewires. The main body guidewire 50 is threaded into the catheter main guidewire lumen at distal tip 36, while the side branch guidewire 54 is threaded into the guidewire channel 4.

The guidewires are fully inserted through the catheter main body lumen and through the guidewire channel, as depicted in FIG. 7. Shown is a main body guidewire 50 fully inserted through the catheter main guidewire lumen and a side branch guidewire 54 fully inserted through the guidewire channel 4.

Step 10) Advance Compressed Device to Target Site

Figure 8:
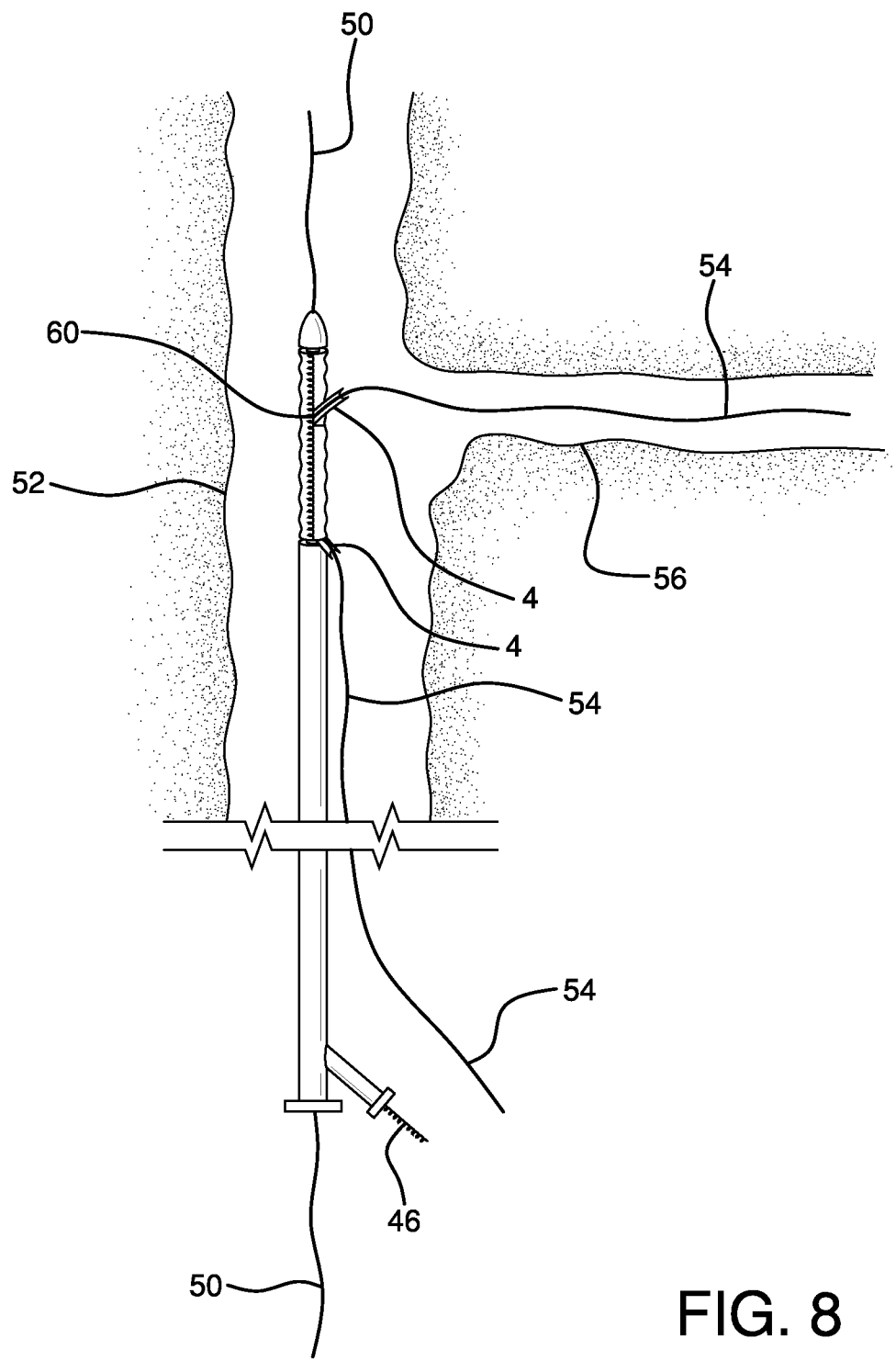
FIG. 8 is a schematic diagram showing a compressed main body stent graft positioned at a branch vessel target site.

The catheter assembly can now be advanced to the target site. As shown in FIG. 8 the catheter and compressed main body device are advanced along the two guidewires 50, 54 until the sheath aperture 60 is aligned to the side branch vessel 56.

Step 11) Release Constraining Sheath to Expand Main Body Device

Figure 9:
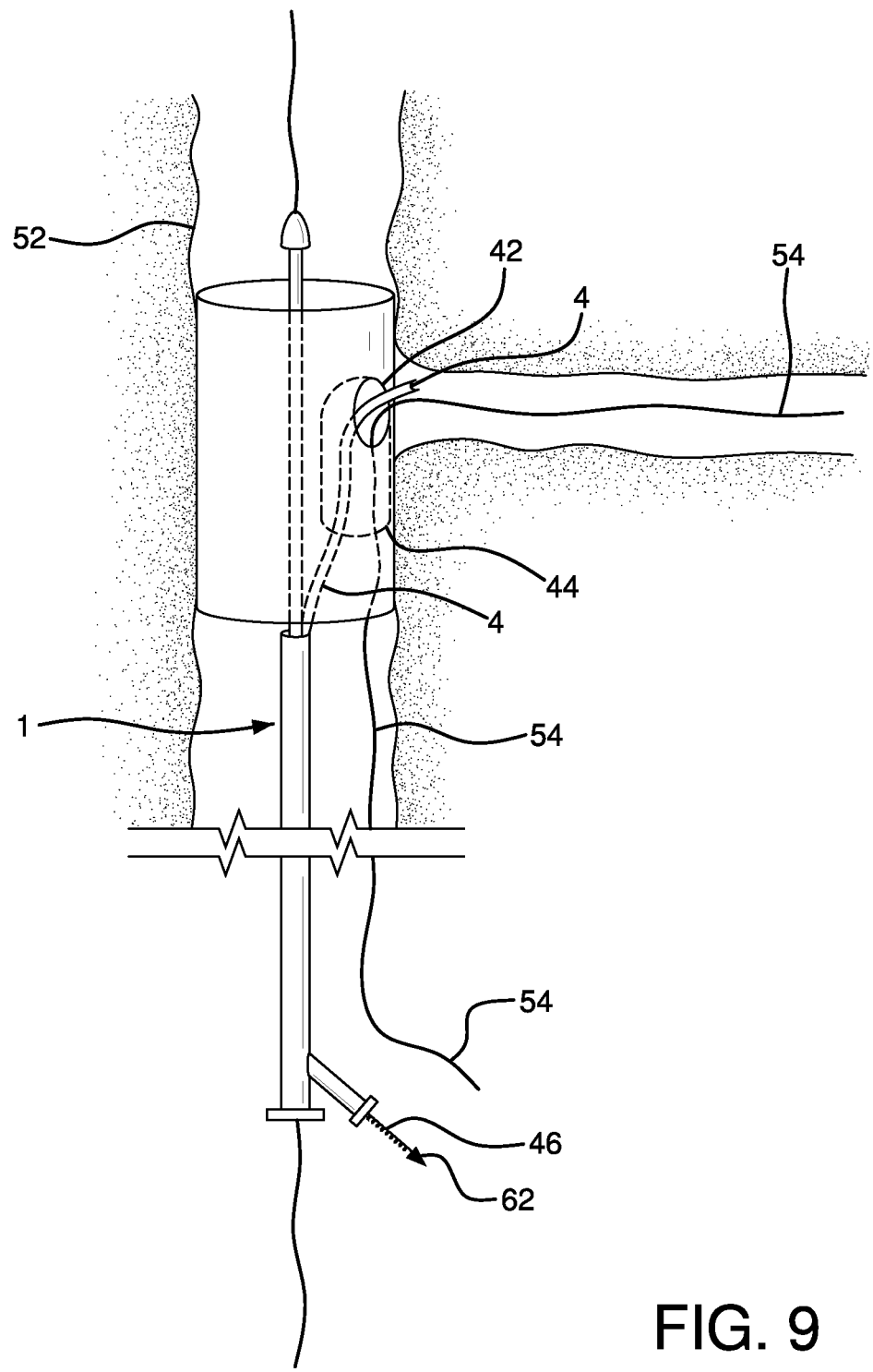
FIG. 9 is schematic diagram showing an expanded main body stent graft having a side branch opening aligned to a side branch vessel.

As shown in FIG. 9, the deployment cord 46 is pulled in the direction shown by arrow 62. By pulling on the deployment cord 46 the constraining sheath is split allowing the main body device 40 to self-expand and engage the main vessel 52. Guidewire 54 will be released from guidewire channel 4 upon expansion of device 40. The constraining sheath (not shown) can be left in-vivo since the sheath will be captured between the main body stent and the main vessel lumen. The side branch guidewire remains routed through the main body side wall opening 42, through the internal side branch support 44 and out through the proximal end of the main body device.

Step 12) Withdraw Catheter from Target Site

The catheter 1 can now be removed, leaving the expanded main body device 40 and the side branch guidewire 54 in place.

Step 13) Backload Side Branch Device onto Side Branch Guidewire.

Figure 10:
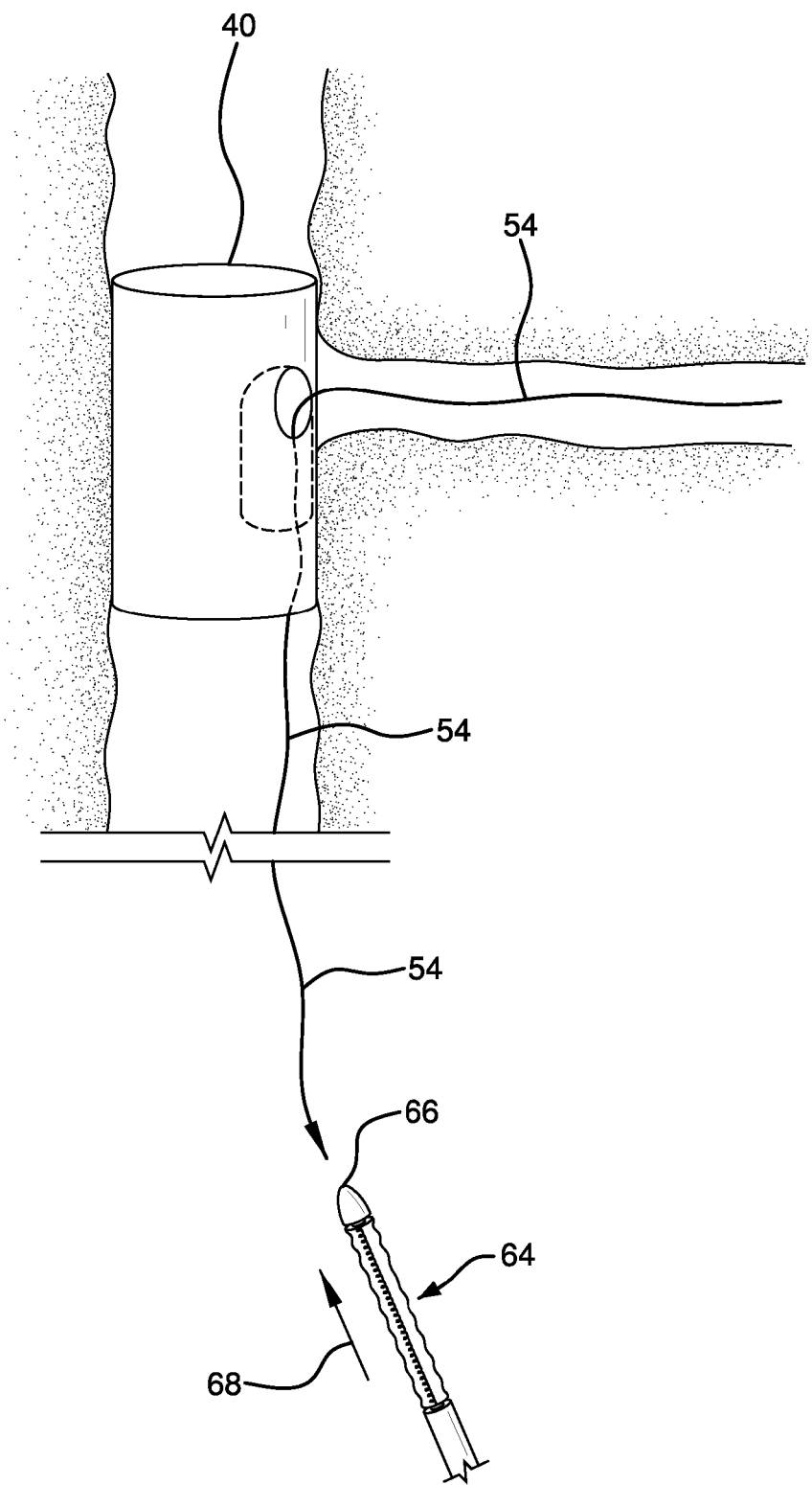
FIG. 10 illustrates the initial advancement of a compressed side branch device.

A compressed side branch stent graft can then be back loaded onto the side branch guidewire. As shown in FIG. 10, the side branch guidewire 54 can be inserted into a side branch guidewire lumen at the distal tip 66 of device 64. The compressed side branch device 64 can then be advanced in the direction indicated by arrow 68. The compressed side branch device can be a stent or stent graft and can be constructed similar to the main body device 40, discussed above.

Figure 11:
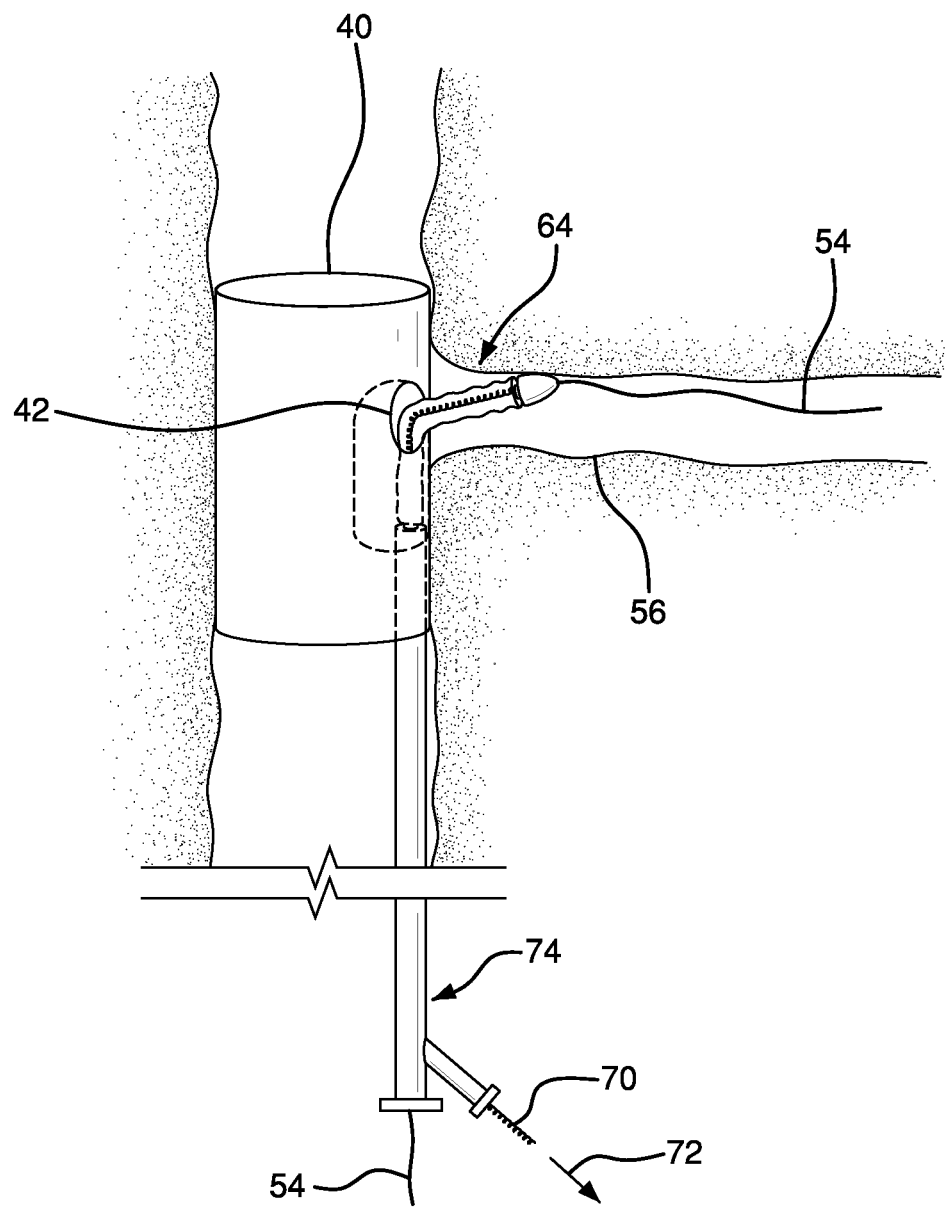
FIG. 11 illustrates a compressed side branch device routed through the main body stent graft and into the side branch vessel.

Step 14) Advance Compressed Side Branch Device Through Internal Side Branch Support Channel As shown in FIG. 11, the compressed side branch device 64 can be fully advanced along guidewire 54 so that the compressed device exits the main body side wall opening 42 and enters the side branch vessel 56.

Step 15) Release Constraining Sheath to Expand Side Branch Device

Figure 12:
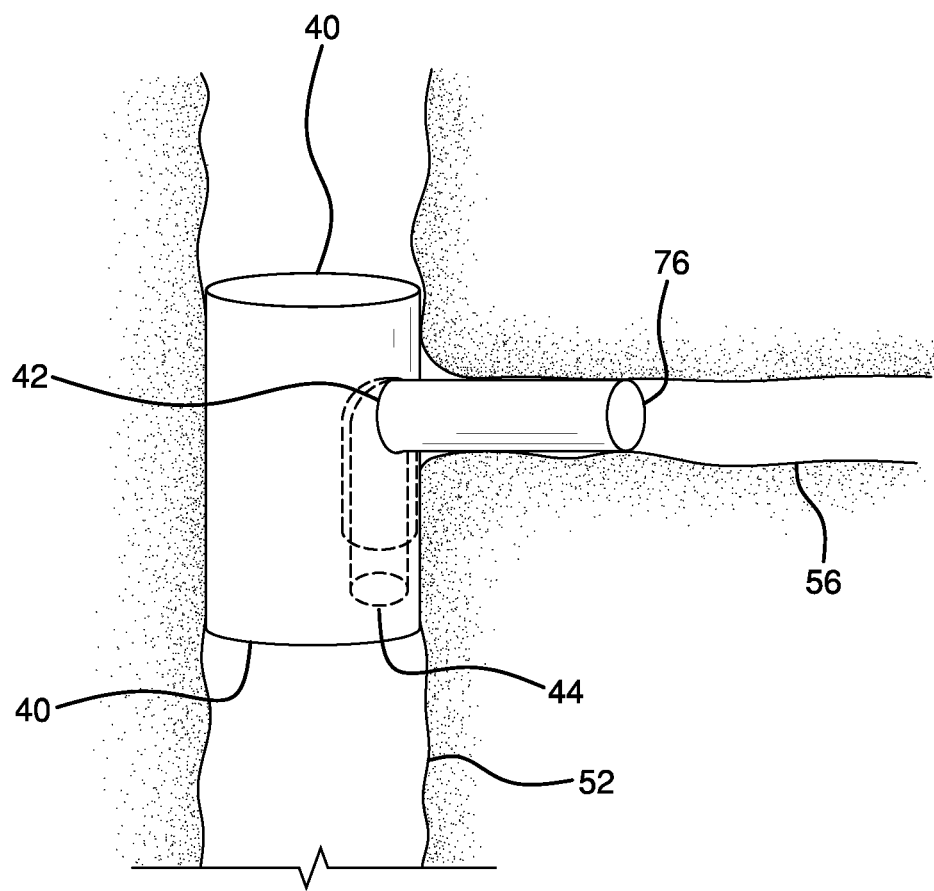
FIG. 12 illustrates a fully deployed main body stent graft and a fully deployed side branch device.

Referring to FIG. 11, the side branch constraining sheath can be released by pulling on the deployment cord 70 along the direction indicated by arrow 72. As shown in FIG. 12, the release of the constraining sheath allows the side branch device 76 to self-expand and engage the side branch vessel 56, the main body side wall opening 42 and the internal side-branch support channel 44. The side branch catheter can be removed after the side branch device is fully expanded. The constraining sheath (not shown) can be left in-vivo since the sheath will be captured in a fashion similar to that of the previous main body device.

The catheter of the invention can be used to deliver an expandable stent graft and expandable side branch device to, for example, the aortic arch branches (arteries of the head, arms, and hands), lower branches of the aorta (celiac), renals, mesenterics, iliacs, the femoral, and lower extremities (legs, feet).

EXAMPLE 1

A catheter having an attached guidewire channel can be fabricated as follows:

1) A self-expanding, main body stent graft can be provided having an outer diameter of 3.1 cm, a length of 15 cm and a graft wall thickness of about 0.005". The graft material can be comprised of ePTFE and FEP and formed from an extruded and expanded thin walled tube that can be subsequently wrapped with ePTFE film. A nitinol wire having a diameter of about 0.0165" can be helically wound to form a stent having an undulating, sinusoidal pattern. The formed, heat-treated stent can be placed onto the base graft. An additional film layer of ePTFE and FEP can be wrapped onto the stent and base graft to selectively adhere the stent to the graft.

2) The main body stent graft can have an internal side-branch support channel formed into the graft wall. Details relating to exemplary fabrication and materials used for an internal side branch support channel can be found in U.S. Pat. No. 6,645,242 to Quinn.

3) A first temporary polymeric tube (PTFE, 0.066" OD) can be placed through the main body stent.

4) A second temporary polymeric tube (PTFE) can be threaded through the main body stent, through the internal side branch support and out through the main body side wall opening.

5) The stent device can be compressed using temporary tethers and a tapered pull-through compression die. The main body stent can be compressed and maintained in the compressed state by a removable constraining sheath.

6) Two wires having 0.038" diameters can be threaded through the first and second polymeric tubes. The polymeric tubes can be removed, leaving the two wires in place, the first through the main body stent and the second through the side branch support.

7) A distal catheter portion with an attached guidewire channel can be provided. The guidewire channel can be formed from a Pebax® 7233 tube having a 0.038" inner diameter and a 0.066" outer diameter. A 0.029" diameter metal wire can be inserted into a 20 cm length of the tube. Using a sharp razor, the tube wall can be skived longitudinally along the top of the internal wire. A channel, having an open width of about 0.036" can therefore be formed along the tube. This 0.036" opening can be sized to allow a 0.035" guidewire to be released from the channel during subsequent device deployment. The channel can be thermally bonded to the proximal end of the distal catheter portion.

The distal catheter portion should not have an enlarged tip so as to facilitate the loading of the compressed device. The compressed device can be transferred onto the distal catheter portion. The attached guidewire channel can be guided over the second wire and through the side branch support. The main catheter shaft can be simultaneously guided over the first wire and through the main body stent. An enlarged tip can be bonded to the distal end of the catheter.

8) The catheter proximal portion and the hub assembly can be bonded together. The deployment cord can be appropriately routed through the proximal catheter and hub assembly. The guidewire channel can be trimmed flush to the constraining sheath.

What is claimed:

1. A catheter comprising:
    a catheter body having a proximal portion, a distal portion, a proximal end including a proximal hub assembly, a distal end, and a deployment line lumen extending between the proximal hub assembly and the distal end of the catheter body;
    a self-expanding prosthesis located at the distal portion of the catheter body, the self-expanding prosthesis having a side opening;
    at least one guidewire channel attached at or near the distal portion of the catheter body, the at least one guidewire channel having proximal and distal ends, the at least one guidewire channel having a length and a longitudinally extending opening therein extending between the at least one guidewire channel proximal end and the at least one guidewire channel distal end, wherein the proximal end of the at least one guidewire channel extends proximally from the self-expanding prosthesis, the longitudinally extending opening being of sufficient width to allow a guidewire to be fully released from the channel during subsequent deployment of the self expanding endoprosthesis;
    a flexible film constraining sheath extending about the self-expanding endoprosthesis for maintaining the self-expanding endoprosthesis toward a delivery configuration suitable for endoluminal delivery and having opposite and spaced apart side edges, the constraining sleeve having a slit located between opposite ends of the sheath and being aligned with the side opening in the self-expanding endoprosthesis; and
    a deployment line extending through the deployment line lumen and releasably coupling the side edges of the constraining sheath to form a longitudinal seam that extends between the opposite ends of the sheath, the longitudinal seam being releasable by decoupling the deployment line and the constraining sheath to allow expansion of the self-expanding endoprosthesis from the delivery configuration,
    wherein the at least one guidewire channel extends for a portion of the length of the constraining sheath, and the distal end of the at least one guidewire channel extends through both the side opening in the self-expanding prosthesis and the slit in the constraining sheath; and
    wherein the slit in the constraining sheath extends transversely to and is in communication with the longitudinal seam, wherein the slit extends through only one of the side edges such that the slit is transverse to and in communication with the longitudinal seam,
    wherein the slit defines a length transverse to the longitudinal seam and a width perpendicular to the length of the slit, wherein the length of the slit is greater than the width of the slit.

2. The catheter of claim 1, wherein the self-expanding prosthesis comprises a stent.

3. The catheter of claim 2, wherein the stent comprises a shape-memory material.

4. The catheter of claim 1, wherein the self-expanding prosthesis comprises a stent graft.

5. The catheter of claim 4, wherein the graft comprises a material selected from the group consisting of ePTFE, nylon, polyester, polyethylene, polypropylene, polytetrafluoroethylene, polyurethane, and elastomeric organosilicon polymers.

6. The catheter of claim 4, wherein the stent graft comprises a first stent at a first open end and a second stent at a second open end of the stent graft.

7. The catheter of claim 6, wherein the graft material extends from the first open end to the second open end.

8. The catheter of claim 4, wherein the stent graft comprises a first open end, a second open end, a side opening, and an internal side branch support.

9. The catheter of claim 8, wherein the internal side branch support extends from the stent graft side opening toward the second open end.

10. The catheter of claim 1, wherein the catheter further comprises a guidewire lumen extending from the catheter distal end to a point proximal thereto.

11. The catheter of claim 1, wherein the at least one guidewire channel comprises a material selected from the group consisting of nylon, polyether block amide, polyurethane, and polyethylene.

12. The catheter of claim 1, further comprising a guidewire configured to be inserted into the at least one guidewire channel.

13. The catheter of claim 1 wherein the at least one guidewire channel cross-sectionally comprises essentially a C-shape.

14. A method for delivering a self-expanding prosthetic device comprising the steps of:
advancing a main body guidewire into a main vessel;
advancing a side branch guidewire into a side branch vessel;
providing a first catheter body having a proximal portion, a distal portion, a proximal end including a proximal hub assembly, a distal end, and a deployment line lumen extending from the distal end to the proximal hub assembly wherein the deployment line lumen contains a deployment line, said catheter body not including a catheter balloon; at least one guidewire channel attached to the distal portion of the catheter body, the channel having a proximal end, a distal end, and a longitudinally extending opening therein extending from the channel proximal end to the channel distal end, the longitudinally extending opening being sized to allow a guidewire to be fully released from the channel during subsequent device deployment; and a self-expanding main body device loaded on the distal portion of the first catheter and contained within a releasable flexible film constraining sheath, the flexible film constraining sheath extending about the self-expanding endoprosthesis for maintaining the self-expanding endoprosthesis toward a delivery configuration suitable for endoluminal delivery and having opposite and spaced apart side edges, the constraining sleeve having a slit located between opposite ends of the sheath and being aligned with the side opening in the self-expanding endoprosthesis, the deployment line extending through the deployment line lumen and releasably coupling the side edges of the constraining sheath to form a longitudinal seam that extends between the opposite ends of the sheath, the longitudinal seam being releasable by decoupling the deployment line and the constraining sheath to allow expansion of the self-expanding endoprosthesis from the delivery configuration, wherein the slit in the constraining sheath extends through only one of the side edges such that the slit is transverse to and in communication with the longitudinal seam;
backloading the lumen of the first catheter and the lumen of the self-expanding main body device onto the main body guidewire;
backloading the at least one guidewire channel onto the side branch guidewire;
advancing the first catheter and the main body device into the main vessel and aligning the side opening with the side branch vessel;
expanding the main body device by the application of tension to a proximal end of the deployment line thereby releasing the constraining sheath; and
removing the first catheter.

15. The method of claim 14, further comprising the steps of:
providing a second catheter having a distal end, a proximal end, a distal portion, a proximal portion, a lumen extending from the distal end to the proximal end, and an expandable side branch device loaded on the distal portion;
advancing the second catheter and the expandable side branch device through the self-expanding main body device, out the side opening, and at least partially into the side branch vessel;
expanding the side branch device; and
removing the second catheter.

16. The method of claim 14, wherein the slit defines a length transverse to the longitudinal seam and a width perpendicular to the length of the slit, wherein the length of the slit is greater than the width of the slit.

* * * * *